(12) United States Patent
Whiteker et al.

(10) Patent No.: US 10,259,789 B2
(45) Date of Patent: Apr. 16, 2019

(54) PROCESS FOR THE PREPARATION OF 4-ALKOXY-3-ACETOXYPICOLINIC ACIDS

(71) Applicant: Dow AgroSciences LLC, Indianapolis, IN (US)

(72) Inventors: Gregory T. Whiteker, Carmel, IN (US); Peter Borromeo, Fishers, IN (US); Fangzheng Li, Carmel, IN (US); Gary Roth, Midland, MI (US)

( * ) Notice: Subject to any disclaimer, the term of this patent is extended or adjusted under 35 U.S.C. 154(b) by 0 days.

(21) Appl. No.: 16/071,512

(22) PCT Filed: Jan. 23, 2017

(86) PCT No.: PCT/US2017/014527
§ 371 (c)(1),
(2) Date: Jul. 20, 2018

(87) PCT Pub. No.: WO2017/127791
PCT Pub. Date: Jul. 27, 2017

(65) Prior Publication Data
US 2019/0047962 A1    Feb. 14, 2019

(51) Int. Cl.
*C07D 213/69* (2006.01)
*C07D 213/79* (2006.01)
*C07D 213/803* (2006.01)

(52) U.S. Cl.
CPC ....... *C07D 213/79* (2013.01); *C07D 213/803* (2013.01)

(58) Field of Classification Search
CPC . C07D 213/69; C07D 213/79; C07D 213/803
USPC ........................................................ 546/296
See application file for complete search history.

(56) References Cited

U.S. PATENT DOCUMENTS

2016/0039760 A1*   2/2016   Grandbois ........... B01J 31/1815
546/327

* cited by examiner

*Primary Examiner* — Taylor V Oh

(57) ABSTRACT

4-Alkoxy-3-hydroxypicolinic acids may be conveniently prepared from 4,6-dibromo-3-hydroxypicolinonitrile in a series of chemical steps selected from bromo substitution, nitrile hydrolysis and halogen reduction that are conducted as a single pot process. 4,6-Dibromo-3-hydroxypicolinonitrile may be prepared from furfural in a series of chemical steps selected from cyano-amination, amine salt formation and bromination-rearrangement. 4-Alkoxy-3-acetoxypicolinic acids may be conveniently prepared from 4-alkoxy-3-hydroxypicolinic acids by treatment with acetic anhydride.

3 Claims, No Drawings

PROCESS FOR THE PREPARATION OF 4-ALKOXY-3-ACETOXYPICOLINIC ACIDS

FIELD

The present disclosure concerns processes for the preparation of 4-alkoxy-3-hydroxypicolinic acids. More particularly, the present disclosure concerns a process for the preparation of 4-alkoxy-3-hydroxypicolinic acids from furfural.

BACKGROUND

U.S. Pat. No. 6,521,622 B1 and U.S. Application Ser. No. 61/747,723 describe inter alia certain heterocyclic aromatic amide compounds of general Formula

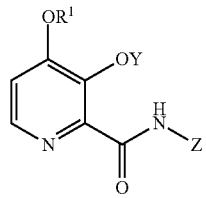

and their use as fungicides.

These disclosures also describe the preparation of 4-alkoxy-3-hydroxypicolinic acids and derivatives thereof as key intermediates in the preparation of these heterocyclic aromatic amide compounds. It would be useful to have an efficient and scalable process route to 4-alkoxy-3-hydroxypicolinic acids from inexpensive raw materials.

SUMMARY

The present disclosure concerns a process for the preparation of 4-alkoxy-3-acetoxypicolinic acids of Formula H

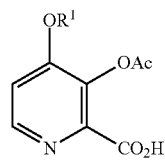

wherein $R^1$ is a $C_1$-$C_3$ alkyl;
from the compound of Formula A

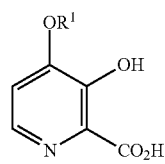

The compound of Formula H may be prepared in a process that comprises the following steps:
 a) creating a mixture containing the compound of Formula A and an acetylating agent; and
 b) isolating the compound of Formula H from the mixture.

Another aspect of the present disclosure is the novel intermediate produced in the present process, viz., the compound:

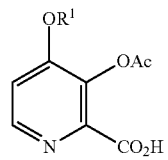

wherein $R^1$ is a $C_1$-$C_3$ alkyl;

DETAILED DESCRIPTION

The terms "isolate," "isolating," or "isolation" as used herein mean to partially or completely remove or separate the desired product from the other components of a finished chemical process mixture using standard methods such as, but not limited to, filtration, extraction, distillation, crystallization, centrifugation, trituration, liquid-liquid phase separation or other methods known to those of ordinary skill in the art. The isolated product may have a purity that ranges from <50% to >50%, and may be purified to a higher purity level using standard purification methods. The isolated product may also be used in a subsequent process step with or without purification.

In the process described herein 4-alkoxy-3-hydroxypicolinic acids are prepared from 4,6-dibromo-3-hydroxypicolinonitrile in a series of chemical steps involving bromo substitution, nitrile hydrolysis, and halogen reduction. The current disclosure describes an improved process for the preparation of 4-alkoxy-3-hydroxypicolinic acids from 4,6-dibromo-3-hydroxypicolinonitrile utilizing a more efficient "one-pot" process.

Also described herein are improved processes for the preparation of 4,6-dibromo-3-hydroxypicolinonitrile from furfural. The processes utilize partial or complete replacement of bromine with a bromide/oxidant pair of reagents that produce bromine in situ. Such a process improvement decreases the need to handle elemental bromine and improves the efficiency of bromine atom utilization.

The in situ generation of bromine in the preparation of 4,6-dibromo-3-hydroxypicolinonitrile from furfural described herein is equivalent to using elemental bromine and surprisingly, the presence of the oxidant does not negatively impact the Strecker or rearrangement reactions. In addition, it was also surprising that the oxidant did not lead to degradation or oxidation of the pyridine ring or the nitrile group of the 4,6-dibromo-3-hydroxypicolinonitrile.

A. Preparation of Compound of Formula A

An improved process for the preparation of 4-alkoxy-3-hydroxypicolinic acids of Formula A from 4,6-dibromo-3-hydroxypicolinonitrile (compound B) utilizing a more efficient "one-pot" process is described. The process involves treating the compound of Formula B first with a sodium alkoxide, and then with zinc metal, aqueous strong base, and optionally, adding additional aqueous strong base, and finally acidifying the final reaction mixture with aqueous strong acid to produce the compound of Formula A (wherein $R^1$ is a $C_1$-$C_3$ alkyl).

In one embodiment of this process, the reaction of the compound of Formula B with sodium methoxide can be conducted in a dipolar, aprotic solvent such as DMSO or sulfolane, optionally with added methanol, or in methanol as the solvent. Utilizing at least 2 molar equivalents of sodium methoxide, preferably 2.5-3 molar equivalents, and heating at from about 50 to about 80° C. for about 1 hour to about 24 hours the displacement of the 4-bromo group with methoxide is complete. The resulting reaction mixture can then be diluted B. Preparation of Compound of Formula B As shown in Scheme II, furfural (Formula D) can be converted in a process using chemical steps a, b and c into 4,6-dibromo-3-hydroxypicolinonitrile (Formula B). The

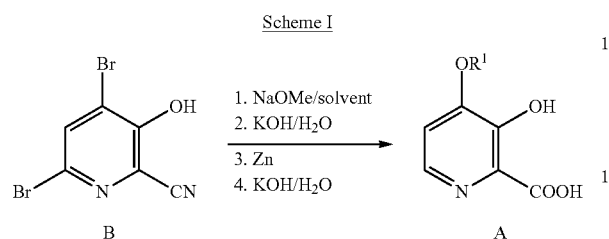

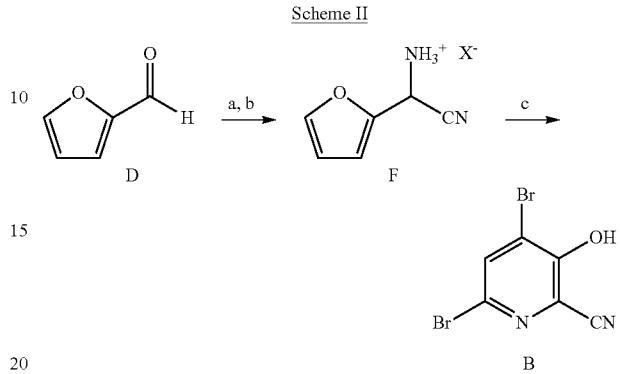

with water and a strong, aqueous base, such as potassium hydroxide or sodium hydroxide (2-3 molar equivalents), treated with from about 1 to about 3 molar equivalents of zinc metal (i.e., Zn dust with a particle size of <10 μm, Zn powder with a particle size of <150 μm, or another high surface area Zn solid) and stirred at from about 20° C. to about 70° C. until reduction of the 6-bromo group is complete. Additional strong aqueous base (2-3 molar equivalents) can then be added and the resulting mixture heated at from about 80° C. to about 95° C. for from about 4 to about 24 hours. The desired compound of Formula A (wherein $R^1$ is methyl) may be isolated by acidifying the reaction mixture and employing standard isolation and purification techniques.

In another embodiment of this process, after the reaction of the compound of Formula B with sodium methoxide is complete, the resulting reaction mixture can then be diluted with water, a strong aqueous base (4-6 molar equivalents), and zinc metal, and then maintained at temperatures ranging from about 20° C. to about 95° C. for from about 2 to about 48 hours. Following completion of the zinc reduction and base hydrolysis reactions, the desired product can be isolated by acidifying the reaction mixture and employing standard isolation and purification techniques.

In another embodiment of this process, after the reaction of the compound of Formula B with sodium methoxide is complete, the resulting reaction mixture can then be diluted with water and strong aqueous base (4-6 molar equivalents), and the resulting mixture heated at from about 80° C. to about 95° C. for from about 4 to about 24 hours to complete hydrolysis of the nitrile group. The resulting mixture can then be treated with zinc metal and then maintained at temperatures ranging from about 20° C. to about 70° C. until reduction of the 6-bromo group is complete. Following completion of the zinc reduction and base hydrolysis reactions, the desired product can be isolated by acidifying the reaction mixture and employing standard isolation and purification techniques.

In another embodiment of this process, after the reaction of the compound of Formula B with sodium methoxide is complete, the hydrolysis of the nitrile group and the reduction of the 6-bromo group may be carried out concurrently by adding the water, the strong aqueous base, and the zinc metal (in one portion or by addition over a period of time) to the reaction vessel and heating it from about 80° C. to about 95° C. for the time needed to complete the hydrolysis of the nitrile group and the reduction of the 6-bromo group.

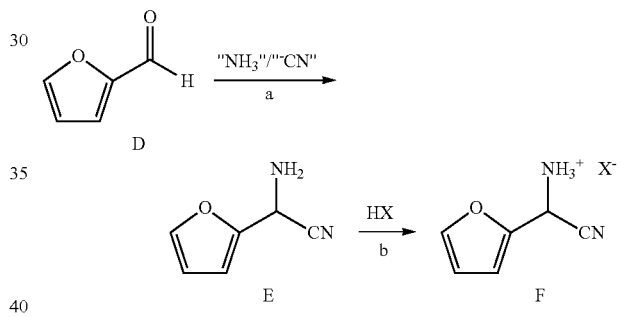

cyano(furan-2-yl)methanaminium halide salt of Formula F is prepared in a biphasic process (organic-aqueous, 2-phase solvent system) by first reacting furfural (Formula D) with at least one equivalent each of an ammonia source and a cyanide source (Step a) in a reaction known in the art as the Strecker synthesis of α-aminonitriles, which is described in *Organic Syntheses*, Coll. Vol. I, page 21 and Coll. Vol. III, pages 84 and 88, to provide the amino(furan-2-yl)acetonitrile of Formula E. Suitable ammonia sources include: ammonium salts such as, but not limited to, ammonium acetate, ammonium bromide, ammonium chloride, ammonium formate, ammonium sulfate and ammonium cyanide; ammonia dissolved in an organic solvent such as, for example, ammonia in methanol, ammonia in ethanol and ammonia in dioxane; ammonia in water (i.e., ammonium hydroxide); and liquid, anhydrous ammonia or gaseous ammonia. Suitable cyanide sources include: cyanide salts such as, but not limited to, sodium cyanide, potassium cyanide and ammonium cyanide; and hydrogen cyanide which may be added in a continuous-addition manner with ammonia to the furfural. The reaction (Step a) is carried out in a 2-phase solvent system consisting of water and a water immiscible solvent selected from: ethers, such as diethyl ether, methyl t-butyl ether (MTBE), tetrahydrofuran (THF), and 2-methyltetrahydrofuran (2-MeTHF); esters, such as ethyl acetate, and isopropyl acetate; alkanes, such as hexane, cyclohexane, heptane, and octane; aromatics, such as anisole, toluene and a xylene or a mixture of xylenes, and mixtures thereof. Such a reaction has been described in WO Application 2000049008, page 55. The present reaction is typically conducted with agitation sufficient to maintain an essentially uniform mixture of the reactants. Such a reaction may be conducted for about 1 to about 50 hours at between about 15° C. and about 30° C.

After the reaction to prepare the amino(furan-2-yl)acetonitrile of Formula E is complete, the organic phase of the 2-phase solvent system containing the compound of Formula E is easily separated from the aqueous phase by standard phase separation and extraction methods. The compound of Formula E, as a solution in the organic phase, is then converted into the salt of Formula F by treatment with an aqueous solution of a mineral acid. Suitable mineral acids include, but are not limited to, hydrobromic acid (HBr), hydrochloric acid (HCl), nitric acid (HNO$_3$), sulfuric acid (H$_2$SO$_4$), and phosphoric acid (H$_3$PO$_4$). The present reaction may be conducted at from about 0° C. to about 25° C. After suitable mixing of the organic phase containing the compound of Formula E and the aqueous solution of the mineral acid, the aqueous acid solution containing the cyano(furan-2-yl)methanaminium halide salt of Formula F is separated from the organic phase by standard phase separation and extraction methods and is ready for the final bromination/rearrangement reaction (Scheme II, Step c) to prepare the compound of Formula B.

In the bromination/rearrangement reaction step of the process, the cyano(furan-2-yl)methanaminium salt of Formula F is treated with a brominating agent, such as bromine, to provide the product of Formula B. The starting material of Formula F, wherein X is Br, Cl,

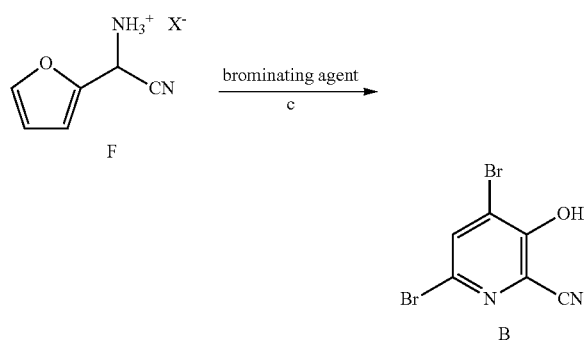

NO$_3$, HSO$_4$, or H$_2$PO$_4$, may be treated with a suitable brominating agent. From about 3 to about 6 molar equivalents of bromine may be used. The reaction is preferably conducted using about 3-5 molar equivalents of bromine and the bromide salt of the compound of Formula F (X=Br). It is often convenient to use an excess of the brominating agent such as a 5%, 10% or 15% molar excess, to insure the reaction proceeds to completion. The reaction is preferably carried out in a protic solvent or reaction medium such as water, or mixtures of water and a water soluble, organic solvent such as, for example, methanol, ethanol, tetrahydrofuran, dioxane or acetonitrile. The temperature at which the reaction is conducted is generally between about 10° C. and about 25° C. Upon completion of the addition of the bromine, the reaction mixture may be allowed to warm slowly to room temperature and stir for 10-48 hours or the reaction may be heated at about 30-40° C. to complete the reaction. Optionally, the reaction time may be shortened by adding a base, such as, for example, 2-4 molar equivalents of sodium acetate, to the reaction. After the reaction is complete the desired product is recovered by employing standard isolation and purification techniques.

In some embodiments of the present disclosure, bromination/rearrangement of the compound of Formula F may involve the use of one or more brominating agents selected from: (1) bromine, and (2) a bromide compound paired with an oxidant. It is known in the literature that bromide compounds such as, for example, HBr, KBr, and NaBr, when combined with an oxidant such as, for example, hydrogen peroxide, potassium peroxymonosulfate (i.e., Oxone®), DMSO or t-butyl hydroperoxide, under appropriate reaction conditions, can produce bromine (this is referred to herein as in situ generation of bromine). Use of a bromide compound that is a salt such as, for example, NaBr or KBr, for the in situ generation of bromine, also requires the use of an acid for bromine formation). The acid may be selected from the group including HBr, HCl, H$_2$SO$_4$, HNO$_3$, H$_3$PO$_4$, acetic acid, and mixtures thereof. Such an approach that involves the in situ generation of bromine offers the advantage of: limiting or eliminating the use of elemental bromine, improving the bromine atom efficiency of the process, and reducing the formation and disposal of bromide waste streams.

In some embodiments of the present disclosure, use of a bromide compound such as, for example, HBr, KBr, or NaBr paired with an oxidant such as hydrogen peroxide in the process to prepare the compound of Formula B from the compound of Formula F (X=Br) can be conducted by slowly adding the hydrogen peroxide (the oxidant) to the compound of Formula F and the bromide compound (i.e., KBr or NaBr as the bromide compound which requires the use of an acid for in situ bromine formation) at ambient temperature and maintaining the temperature at less than about 50° C. during the addition. From about 3-5 molar equivalents of hydrogen peroxide relative to the compound of Formula B may be used in the presence of a sufficient amount of the bromide compound (2-5 molar equivalents) and an acid in the process.

Chemical literature describing the use of bromide compounds with oxidants to conduct bromination chemistry include: a) "Simple and Practical Halogenation of Arenes, Alkenes, and Alkynes with Hydrohalic Acid/H2O2 (or TBHP)," *Tetrahedron*, 55, (1999) 1127-1142, b) "Oxidative Halogenation with "Green" Oxidants: Oxygen and Hydrogen Peroxide," *Angew. Chem. Int. Ed.*, 2009, 48, 8424, and references therein. Patents describing the generation of bromine from the reaction of bromide salts or HBr with hydrogen peroxide include U.S. Pat. Nos. 5,266,295, 4,029, 732 and 2,772,302.

C. Preparation of Compound of Formula G

Another embodiment of the present disclosure involves a process for the preparation of the compound of Formula G from furfural. In the first part of this process, furfural is converted into the cyano(furan-2-yl)methanaminium bromide salt of Formula F (X is Br), using the biphasic process as described herein. In the next step of the process, the bromide salt of Formula F is combined with additional aqueous HBr (1.5 equivalents) and then reacted with from about 3 to about 4 molar equivalents of hydrogen peroxide (relative to the bromide salt of Formula F) to provide 3-hydroxy-picolinonitrile (Formula G). The temperature at

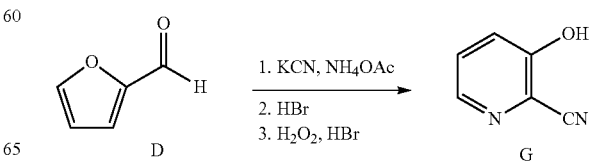

which the hydrogen peroxide addition may be conducted is between about 0° C. and about 50° C. Upon completion of the addition of the hydrogen peroxide, the reaction mixture is allowed to stir at room temperature for about one to about 24 hours. After the reaction is complete, the desired product is recovered by employing standard isolation and purification techniques.

D. Preparation of Compound of Formula H

The conversion of the 4-alkoxy-3-hydroxypicolinic acid of Formula A to the 3-acetoxy compound of Formula H, may be accomplished by acetylating the compound of Formula A with one or more acetylation reagents selected from acetic anhydride and acetyl chloride, bases selected from pyridine, alkyl substituted pyridines, and trialkylamines, or utilization of Schotten-Baumann reaction conditions.

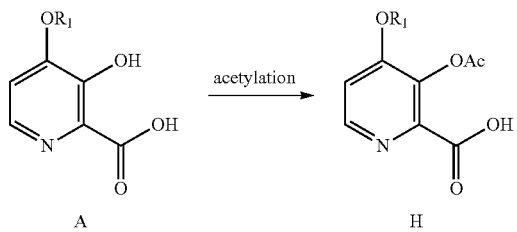

The product obtained by any of these processes, can be recovered by conventional means, such as evaporation, filtration or extraction, and can be purified by standard procedures, such as by recrystallization or chromatography.

The following examples are presented to illustrate the disclosure.

EXAMPLES

Example 1a. 3-Hydroxy-4-methoxypicolinic Acid

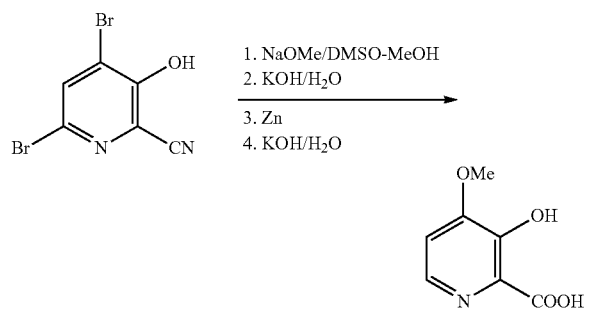

A slurry of sodium methoxide (25 g, 0.45 mol) was prepared with 50 mL of anhydrous DMSO and 1 mL of MeOH. To this slurry was added a solution of 4,6-dibromo-3-hydroxy-2-picolinonitrile (50 grams, 0.181 mol) and about 50 mL of anhydrous DMSO, which was added over 30 minutes. The reaction was maintained between 50-65° C. during the addition. After the addition was complete, the reaction was allowed to stir for an additional hour at >50° C. The reaction was determined to be complete by $^1$H NMR analysis. The reaction was allowed to cool to 35° C., and then 100 mL of water, followed by 45% KOH (40 mL, 468 mmol) were added to the reaction solution. Zinc dust (15.4 g 234 mmol; <10 micron particle size) was then added in 5 gram portions at 15 min intervals, which led to a temp rise to about 45° C. The reaction was allowed to stir overnight at ambient temperature. The reaction was not complete, so the reaction was heated to 50° C., and then additional Zn dust (4.8 grams, 74 mmol) was added. The reaction was complete after 3 hours. Additional KOH (45% aqueous, 40 mL, 468 mmol) was added to the reaction mixture. The reaction was then heated at 94° C. for 12 hours to complete the hydrolysis. The reaction was cooled to ambient, and then filtered to remove solids. The solids were washed with about 100 mL of water into the reaction solution. The pH of the combined filtrate and wash solution was then adjusted to 0.4 with 12N HCl. The resulting mixture was allowed to stir for about 1 hour to ensure the pH was stable, and then the solids were collected by filtration. The resulting off-white solids were washed with acetone. The material was dried in a vacuum oven at 50° C. to afford 4-methoxy-3-hydroxypicolinic acid as a very pale yellow powder (19.22 g, 63.2% yield with 96% purity, which equates to 60.7% yield). The organic purity was 99.75% as determined by HPLC. $^1$H NMR (400 MHz, DMSO-d$_6$) δ 8.03 (d, J=6.4 Hz, 1H), 7.39 (d, J=6.4 Hz, 1H), 4.04 (s, 3H).

Example 1b. 3-Hydroxy-4-methoxypicolinic Acid

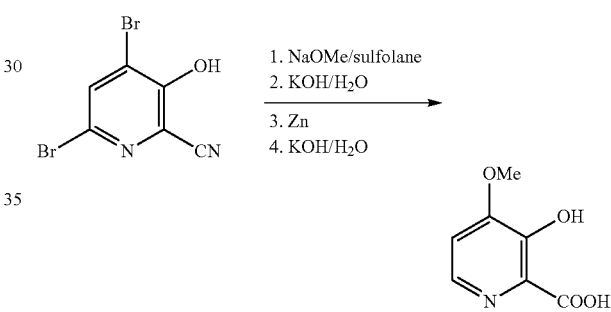

Neat sodium methoxide (14.7 g, 271 mmol) was added to a solution of 4,6-dibromo-3-hydroxypicolinonitrile (30.2 g, 109 mmol) and sulfolane (120 g) over a 30 minute period, which led to a temperature rise to 50° C. The reaction was then heated at 60° C. for 18 hours. The reaction solution was allowed to cool to ambient temperatures, and then 150 mL of DI water was added to the reaction, followed by 50 mL of 45 wt % KOH (5.4 equiv, 586 mmol). Zn dust (113 mmol, 7.5 grams) was added, and then the reaction was heated to 40° C. After 2 hours, additional Zn dust (2.5 grams, 38 mmol) was added, and then the reaction was heated to 60° C. for an additional 2 hours. The reaction was allowed to stir overnight at ambient. $^1$H NMR analysis of the reaction mixture indicated that the debromination was complete. The reaction was filtered to remove solids, 45% KOH (50 mL, 596 mmol) was added to the filtrate, and then the resulting solution was heated to about 90° C. The reaction was allowed to stir at about 90° C. for 5.5 h, which resulted in near complete conversion. The reaction was allowed to stir at about 90° C. overnight. The reaction mixture was cooled to <30° C., and then the pH was adjusted to 0.8 with 40% sulfuric acid, which led to the formation of solids. The solids were isolated by filtration and then dried to yield a solid, which was greater than a 100% yield. The material was slurried overnight in 0.5 pH hydrochloric acid. The material was then isolated by filtration and drying to afford 10.3 grams of 4-methoxy-3-hydroxypicolinic acid as an off-white powder, which was determined to be 94% pure by HPLC (53% yield).

Example 1c. 3-Hydroxy-4-methoxypicolinic Acid

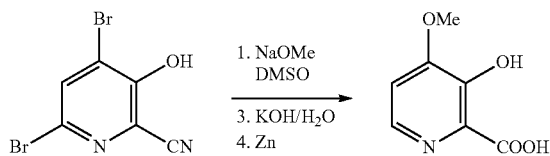 [SMILES: N#Cc1nc(Br)cc(Br)c1O ; COc1ccnc(C(=O)O)c1O]

A 500 mL 3-neck flask was charged with sodium methoxide (25 g, 0.462 mol) and 25 mL of dimethyl sulfoxide. The sodium methoxide/DMSO mixture was placed under inert gas and mechanically stirring to create a free flowing slurry. A solution of 4,6-dibromo-3-hydroxypicolinonitrile (50.3 grams, 0.181 mol, DBHP, 96.2 wt % purity) in about 25 mL of anhydrous DMSO was prepared in a separate vessel. The DBHP solution was added to the sodium methoxide/DMSO mixture over 50 minutes via a syringe pump. The temperature was maintained below 60° C. during the addition. After the addition was complete, the reaction was allowed to stir for an additional hour. During that time the reaction mixture solidified. 100 mL of water followed by 50% KOH (50 mL, 941 mmol) were added to the solidified reaction mixture. The resulting mixture was stirred for about 1.5 hours to break up the solids into a thick slurry. Zn dust (14.8 g, 226 mmol) was then added in about 5 gram portions about 20 minutes apart, which led to a temperature rise to about 40° C. Over the course of the Zn digestion, the reaction thinned into an easily mixed slurry. The reaction was allowed to stir overnight at ambient temperature. The reaction was then heated up to 95° C. for 24 hours. The reaction was cooled to <20° C., and then the pH of the solution was adjusted to 0.6 with aqueous HCl (12 N), which resulted in the precipitation of the product. The solids were isolated by filtration, washing with about 50 mL of water, and then washed with about 25 mL of acetone. The resulting slightly yellow powder was allowed to dry in the hood, which led to 23.3 grams of product. The product was 96% pure as determined by $^1$H NMR (versus internal standard), which equated to a 76% yield of the desired product based on the purity of the starting material and final product. $^1$H NMR (400 MHz, DMSO-$d_6$) δ 8.03 (d, J=6.4 Hz, 1H), 7.39 (d, J=6.4 Hz, 1H), 4.04 (s, 3H).

Example 1d. Cyano(furan-2-yl)methanaminium Bromide

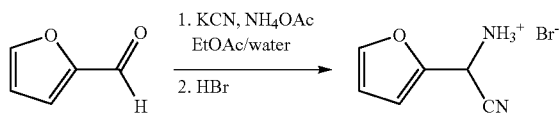 [SMILES: O=Cc1ccco1 ; N#CC([NH3+])c1ccco1 ; [Br-]]

To an 500 mL flask outfitted with a stir bar was added 33.65 grams of ammonium acetate (436 mmol), 150 mL of ethyl acetate, 30 mL of DI water, and 10 grams of KCN (154 mmol). Furfural (14 g, 145 mmol) was then added to the reactor via syringe. The temperature in the reactor increased from about 15° C. to 24° C. The reaction was allowed to stir overnight at ambient. $^1$H NMR analysis of the ethyl acetate phase showed that the conversion was >95% complete. 75 mL of 20% aqueous sodium carbonate was added to the reactor and allowed to stir for 10 minutes. The sodium carbonate solution was removed and then the reaction mixture was washed with 40 mL of saturated brine. $^1$H NMR (400 MHz, DMSO-$d_6$) δ 7.53 (dd, J=2.0, 1.0 Hz, 1H), 6.47 (dd, J=3.4, 1.1 Hz, 1H), 6.42 (dd, J=3.3, 1.7 Hz, 1H), 5.08 (s, 1H).

After removal of the brine phase, 24.5 mL of aqueous 48% HBr (1 equiv., 145 mmol) diluted in about 130 ml of DI water was added to the reaction. The reaction was mixed for 15 minutes. The aqueous layer was removed and placed in a separate vessel. The organic layer was then washed with 2×25 mL of DI water. Each wash was added to the holding vessel with the initial HBr extracted phase. A total of 210.5 grams of aqueous phase was obtained containing about 14.06 wt % of cyano(furan-2-yl)methanaminium bromide.

Example 1e. 4,6-Dibromo-3-hydroxypicolinonitrile

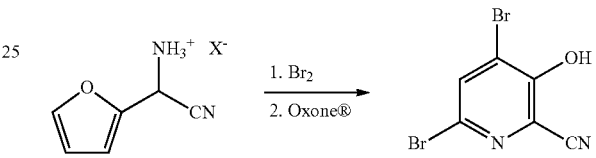

52.5 g of the aqueous phase containing 7.38 g (36 mmol) of cyano(furan-2-yl)methanaminium bromide (14.06 wt % in water) was placed into a 250 mL flask outfitted with a stir bar. The flask was then placed in an ice bath. After cooling to <10° C., 5.8 g of bromine (36 mmol) was then added to the reaction drop wise over 15 minutes resulting in the formation of solids. After stirring for 1 h the reaction was allowed to warm to ambient temperature. Oxone® (27 g, 87.8 mmol) was added to the reaction in portions resulting in the dissolution of the solids and a reddish brown liquid phase, which slowly converted to round pellet-like material after stirring for 1 h. The reaction was quenched with saturated, aqueous sodium bisulfite. The solids were then isolated by filtration, washed with DI water, and then dried overnight to yield 6.25 grams of a tan powder. $^1$H NMR analysis indicated that the product consisted of 4,6-dibromo-3-hydroxypicolinonitrile (96.6 mol %, 60.3% yield) and 6-bromo-3-hydroxypicolinonitrile (3.4 mol %, 2.2% yield). $^1$H NMR (400 MHz, DMSO-$d_6$) δ 8.27 (s, 1.00H), 7.75 (d, J=8.9 Hz, 0.034H), 7.44 (d, J=8.9 Hz, 0.034H). HRMS (m/z) Positive Ion mode [M+1] calcd for $C_6H_3Br_2N_2O$ 276.8612; found 276.8611.

Example 1f. 4,6-Dibromo-3-hydroxypicolinonitrile

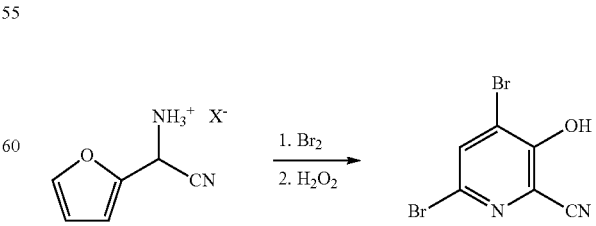

52.5 g of the aqueous phase containing 7.38 g (36 mmol) of cyano(furan-2-yl)methanaminium bromide (14.06 wt % in water) was placed into a 250 mL flask outfitted with a stir bar. The flask was then placed in an ice bath. After cooling to <10° C., 5.8 g of bromine (36 mmol) was then added to the reaction drop wise over about 15 minutes resulting in the formation of solids. After stirring for 1 h, 30% hydrogen peroxide (9.4 mL) was added to the reaction via syringe over 20-30 minutes. This resulted in the dissolution of the solids and then precipitation of a fine powder over a 1-2 hour period. The reaction was quenched with saturated sodium bisulfite. The solids were then isolated by filtration, washed with DI water, and then dried overnight to yield 6.03 grams of a tan powder. $^1$H NMR analysis indicated that the product consisted of 4,6-dibromo-3-hydroxypicolinonitrile (94.5 mol %, 57.3% yield) and 6-bromo-3-hydroxypicolinonitrile (5.5 mol %, 3.2% yield). $^1$H NMR (400 MHz, DMSO-$d_6$) δ 8.27 (s, 1.00H), 7.75 (d, J=8.9 Hz, 0.075H), 7.44 (d, J=8.9 Hz, 0.075H). $^{13}$C NMR (101 MHz, DMSO-$d_6$) δ 157.65, 141.95, 135.55, 128.76, 124.37, 120.34, 115.97. HRMS (m/z) Positive Ion mode [M+1] calcd for $C_6H_3Br_2N_2O^+$ 276.8612; found 276.8609.

Example 1g. 3-Hydroxypicolinonitrile

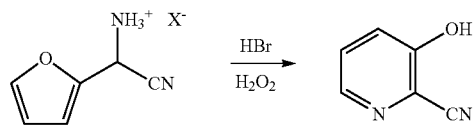

52.5 g of the aqueous phase containing 7.38 g (36 mmol) of cyano(furan-2-yl)methanaminium bromide (14.06 wt % in water) was placed into a 250 mL flask outfitted with a stir bar. 48% HBr (6.2 mL, 55 mmol) was added to the flask with stirring. The flask was then placed in an ice bath. After cooling to <5° C., about 7 mL of 30% hydrogen peroxide was added to the reaction via syringe over 20-30 minutes. This resulted in very little heat evolution. The reaction was allowed to warm to ambient temperature, at which point the reaction started to self heat to about 50° C. The reaction was cooled to 20° C., and then 7 mL of 30% peroxide was added, which resulted in the formation of a precipitate. The reaction was allowed to stir for about 20 min and then the reaction was quenched with saturated sodium bisulfite, which resulted in a temperature rise to about 40° C. During the temp rise, the solids dissolved. The reaction was then placed in an ice bath. After stirring for about 45 minutes, solids developed. The solids were collected by filtration and washed with DI water. 3-Hydroxypicolinonitrile (1.63 grams) was isolated as a tan crystalline solid (37.3% yield). $^1$H NMR (400 MHz, DMSO-$d_6$) δ 11.67 (s, 1H), 8.19 (dd, J=4.4, 1.3 Hz, 1H), 7.56 (dd, J=8.6, 4.4 Hz, 1H), 7.47 (dd, J=8.7, 1.4 Hz, 1H). $^{13}$C NMR (101 MHz, DMSO-$d_6$) δ 157.67, 141.93, 135.56, 128.75, 125.99, 124.37, 120.34, 115.97. HRMS (m/z) Negative Ion mode [M−1] calcd for $C_6H_4N_2O$ 119.0246; found 119.0240.

Example 1h. 4,6-Dibromo-3-hydroxypicolinonitrile

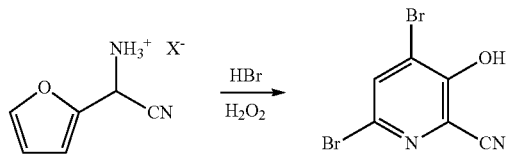

53 g of the aqueous phase containing 7.45 g (37 mmol) of cyano(furan-2-yl)methanaminium bromide (14.06 wt % in water) was placed into a 250 mL flask outfitted with a stir bar. 48% HBr (8.2 mL, 73 mmol) was added to the flask with stirring. The flask was placed in an ice bath. After cooling to <5° C., 6 to 7 mL of 30% hydrogen peroxide was added to the reaction via syringe over 20-30 minutes. This resulted in very little heat evolution. The reaction was allowed to warm to ambient temperature, at which point the reaction started to self heat to about 46-48° C. and became yellow orange in color (homogeneous). The reaction was cooled to 20° C., and then another 7 mL of the 30% hydrogen peroxide was added via syringe over 15-20 minutes, which resulted in the formation of a precipitate. The reaction was allowed to stir overnight. The reaction was quenched with sodium bisulfite to yield a slightly yellow solution with solids. Peroxide test strips indicated no residual peroxides. The solids were collected by filtration, washed with water, and dried to yield 6.22 grams of a light tan powder. $^1$H NMR analysis indicated that the product consisted of 4,6-dibromo-3-hydroxypicolinonitrile (58.1% yield) and 6-bromo-3-hydroxypicolinonitrile (3.8% yield). $^1$H NMR (400 MHz, DMSO-$d_6$) δ 8.27 (s, 1.00H), 7.75 (d, J=8.9 Hz, 0.064H), 7.44 (d, J=8.9 Hz, 0.064H).

Example 1i. 4,6-Dibromo-3-hydroxypicolinonitrile

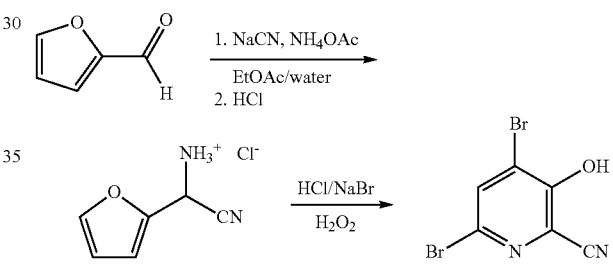

A stock solution of cyano(furan-2-yl)methanaminium chloride was prepared using 39.21 grams of furfural, 20 grams of sodium cyanide, 96 grams of ammonium acetate in 300 mL of ethyl acetate and 260 mL of water. After formation of the α-aminonitrile, 75 mL of saturated sodium carbonate was added to the mixture and allowed to mix for 20-30 minutes. The aqueous phase was removed and then the organic phase was subsequently washed with 2×50 mL of saturated aqueous brine. 34 mL of aqueous 12 N HCl (1 equiv., 408 mmol) diluted in about 260 ml of DI water was added to the organic phase. The resulting mixture was mixed (>500 rpm) for 15 minutes. After settling, the aqueous layer containing the cyano(furan-2-yl)methanaminium chloride was removed and placed in a plastic holding vessel to form a stock solution. The organic layer was then extracted with 44 mL of DI water, followed by 46 mL of DI water. Each aqueous extract was placed in the holding vessel resulting in about 460 g of aqueous phase. The aqueous phase was diluted to a total of 480 grams which contained about 64.70 g (13.5 wt %) of the cyano(furan-2-yl)methanaminium chloride.

60 grams of the stock solution containing about 8.1 g (51 mmol) of cyano(furan-2-yl)methanaminium chloride was placed into a 250 mL RB flask with a stir bar. About 4.2 mL (50.4 mmol) of 12N HCl and 10.4 g (101 mmol) of NaBr were added to the flask. 30% hydrogen peroxide (20 g, 176 mmol) was added dropwise over 50 minutes to the flask.

Over a 25 min period during the addition (about 7.5 g of peroxide had been added), the reaction self heated to 56° C., at which point the reaction was cooled to about 36° C. After 40 minutes, solids began to form. The reaction was allowed to stir for an additional 6 hours. The solids were collected by filtration, washed with DI water, and then dried. 6.28 grams of a free flowing, light tan powder was obtained as a mixture of 4,6-dibromo-3-hydroxypicolinonitrile (39.1 wt % yield), 6-bromo-3-hydroxypicolinonitrile (3.0 wt % yield), 6-chloro-3-hydroxy-picolinonitrile (6.23 wt % yield), and one of the 4/6-chloro/bromo-3-hydroxypicolinonitrile isomers (0.4 wt % yield) as determined by $^1$H NMR. A total yield of 51% was observed. $^1$H NMR (400 MHz, DMSO-d$_6$) of the desired product: δ 8.27 (s, 1.00H), δ 8.18 (s, 0.11H), δ 7.75 (d, J=8.9 Hz, 0.64H), 7.65 (d, J=8.9 Hz, 0.01H), 7.53 (d, J=8.9 Hz, 0.01H), 7.44 (d, J=8.9 Hz, 0.064H).

Example 1j. 4,6-Dibromo-3-hydroxypicolinonitrile

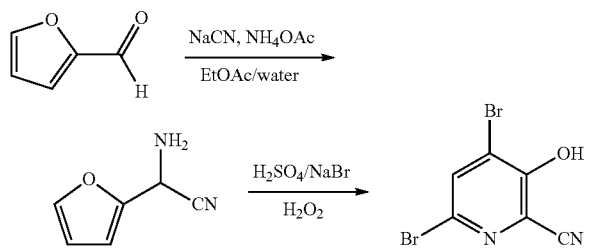

To a 500 mL flask outfitted with a stir bar was added 36 grams of ammonium acetate (467 mmol), 200 mL of ethyl acetate, and 7.5 grams of NaCN (153 mmol). 75 mL of water was utilized to wash the residual sodium cyanide into the flask and out of the funnel. Furfural (12.7 mL, 14.7 grams, 153 mmol) was then quickly added to the reactor via syringe. The temperature in the reactor increased from about 15° C. to 24° C. The reaction was allowed to stir overnight at ambient temperature (18° C.). The agitation was turned off to allow the two liquid phases to separate. The organic phase was then sampled for $^1$H NMR analysis and the reaction was determined to be only about 80% complete. The reaction was then stirred at 25° C. (using a water bath) for an additional 6 hours. The reaction was shown to be about 90% complete by $^1$H NMR. 75 mL of 20% aqueous sodium carbonate was added to the reactor and allowed to stir for 30 minutes, and then the mixture was allowed to sit without stirring for 20-30 min. The aqueous phase was removed and then the organic phase containing the α-aminonitrile of furfural in ethyl acetate was washed with 2×50 mL of saturated brine.

10 N sulfuric acid (15 mL, 1 equivalent, 153 mmol) was diluted in about 225 ml of DI water. The ethyl acetate solution containing the α-aminonitrile of furfural was extracted with the diluted sulfuric acid solution in about 1/3 portions. Each extraction was placed into a 500 mL RB with a stir bar. The organic solution was extracted with an additional 5 mL of DI water. To the combined aqueous acid extracts was added 47 g of sodium bromide (459 mmol) and then hydrogen peroxide (30%, 360 mmol) was added over a 2 hour period, which resulted in a temperature rise from 19° C. to about 50° C. The reaction was allowed to stir overnight. $^1$H NMR analysis indicated that the reaction was a 1:1 mixture of 6-bromo-3-hydroxypicolinonitrile and 4,6-dibromo-3-hydroxypicolinonitrile. An additional 15 mL of 10 N sulfuric acid and 13.5 grams of 30% peroxide (107 mmol) was added to the reaction solution and the reaction was heated to 45° C. After 2 hours, the reaction was complete as indicated by $^1$H NMR analysis. The solids were collected by filtration, washed with water, and dried to yield 21.9 grams of a light tan powder. $^1$H NMR analysis indicated that the powder consisted of 4,6-dibromo-3-hydroxypicolinonitrile (49.8% yield) and 6-bromo-3-hydroxypicolinonitrile (2.4% yield).

Example 1k. 3-(Acetyloxy)-4-methoxypicolinic Acid

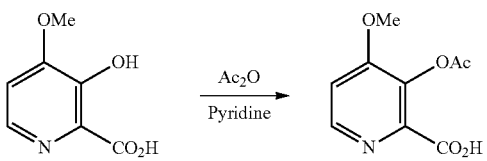 [SMILES: "Ac2O" ; COc1ccnc(C(=O)O)c1O ; "Pyridine" ; COc1ccnc(C(=O)O)c1OC(C)=O]

3-Hydroxy-4-methoxypicolinic acid (5.0 g, 29.6 mmol) was slurried in 50 mL of pyridine and 50 mL of acetic anhydride at ambient temperature. After 1 h, a yellow solution had formed which was then stirred overnight. The solution was evaporated at 45° C. (2 mm Hg) to give 6.28 g of tan solid (99% yield, mp=132-134° C.). $^1$H NMR (400 MHz, DMSO-d$_6$) δ 13.32 (s, 1H), 8.43 (d, J=5.5 Hz, 1H), 7.40 (d, J=5.5 Hz, 1H), 3.91 (s, 3H), 2.27 (s, 3H). $^{13}$C NMR (101 MHz, DMSO-d$_6$) δ 167.95, 164.81, 158.34, 147.87, 142.77, 136.18, 110.87, 56.59, 20.27. HRMS (m/z) calcd for C$_9$H$_9$NO$_5$ 211.0478, found 211.0481 ([M]+).

What is claimed is:

1. A process for the preparation of a compound of Formula H

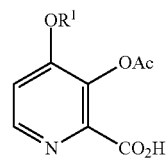

wherein R$^1$ is a C$_1$-C$_3$ alkyl;
from a compound of Formula A

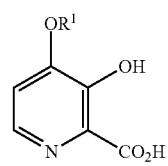

which comprises the following steps:
a) creating a mixture containing the compound of Formula A and an acetylating agent; and
b) isolating the compound of Formula H from the mixture.
2. The process of claim 1 wherein the acetylating agent is selected from acetic anhydride and acetyl chloride.

3. A compound of formula
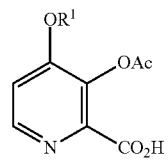
wherein $R^1$ is a $C_1$-$C_3$ alkyl.
* * * * *